United States Patent
Kim et al.

(10) Patent No.: US 10,537,014 B2
(45) Date of Patent: Jan. 14, 2020

(54) COMPOSITION FOR OBESITY TREATMENT COMPRISING LIQUID-PHASE PLASMA

(71) Applicant: AJOU UNIVERSITY INDUSTRY-ACADEMIC COOPERATION FOUNDATION, Suwon-si (KR)

(72) Inventors: Chul Ho Kim, Seoul (KR); Sung Un Kang, Suwon-si (KR)

(73) Assignee: AJOU UNIVERSITY INDUSTRY-ACADEMIC COOPERATION FOUNDATION, Gyeonggi-Do (KR)

( * ) Notice: Subject to any disclaimer, the term of this patent is extended or adjusted under 35 U.S.C. 154(b) by 0 days.

(21) Appl. No.: 16/335,925

(22) PCT Filed: Sep. 19, 2017

(86) PCT No.: PCT/KR2017/010234
§ 371 (c)(1),
(2) Date: Mar. 22, 2019

(87) PCT Pub. No.: WO2018/056664
PCT Pub. Date: Mar. 29, 2018

(65) Prior Publication Data
US 2019/0313520 A1  Oct. 10, 2019

(30) Foreign Application Priority Data

Sep. 22, 2016  (KR) .................. 10-2016-0121357
Aug. 11, 2017  (KR) .................. 10-2017-0102295

(51) Int. Cl.
*H05H 1/24* (2006.01)
*A61P 3/04* (2006.01)
*A61K 9/00* (2006.01)

(52) U.S. Cl.
CPC ............. *H05H 1/24* (2013.01); *A61K 9/0053* (2013.01); *A61P 3/04* (2018.01)

(58) Field of Classification Search
CPC ...... H05H 1/24; A61K 9/0053; A61K 9/0019; A61K 9/0014; A61P 3/04; Y10S 514/909; A61N 1/44
See application file for complete search history.

(56) References Cited

U.S. PATENT DOCUMENTS

2005/0101016 A1    5/2005  McIntyre
2012/0094250 A1*   4/2012  Lloyd .................. A61C 19/06
                                                              433/80

(Continued)

FOREIGN PATENT DOCUMENTS

JP    2015084290    4/2015
KR    20080004452   1/2008

(Continued)

OTHER PUBLICATIONS

International Search Report—PCT/KR2017/010234 dated Feb. 19, 2018.

(Continued)

Primary Examiner — Daniel D Chang
(74) Attorney, Agent, or Firm — Cantor Colburn LLP

(57) ABSTRACT

Provided is a composition for obesity treatment comprising a liquid-phase plasma. More particularly, provided is a method for producing a liquid-phase plasma for inhibiting adipocyte differentiation or proliferation, a pharmaceutical composition for obesity prevention or treatment using a liquid-phase plasma produced according to the method, and a method for obesity prevention or treatment using the liquid-phase plasma.

10 Claims, 13 Drawing Sheets

Specification includes a Sequence Listing.

(56) References Cited

U.S. PATENT DOCUMENTS

2013/0109838 A1     5/2013    McIntyre
2019/0313520 A1*   10/2019   Kim .......................... A61P 3/04

FOREIGN PATENT DOCUMENTS

| KR | 101248668 | 3/2013 |
| KR | 20130099522 | 9/2013 |
| KR | 20150084146 | 7/2015 |
| KR | 101577207 | 12/2015 |
| KR | 101657063 | 9/2016 |
| WO | 2016096751 | 6/2016 |

OTHER PUBLICATIONS

Brun, et al., Adipocyte differentiation: a transcriptional regulatory cascade, Cell Differentiation, 1996, pp. 826-832.

Darlington, et al., The Role of C/EBP Genes in Adipocyte Differentiation, The Journal of Biological Chemistry, 1998, pp. 30057-30060.

Jessen, et al., Expression profiling during adipocyte differentiation of 3T3-L1 fibroblasts, GENE an International Journal on Genes and Genomes, 2002, pp. 95-100.

Osborne, Sterol Regulatory Element-binding Proteins (SREBPs): Key Regulators of Nutritional Homeostasis and Insulin Action, The Journal of Biological Chemistry, 2000, pp. 32379-32382.

Rosen, et al., Molecular Regulation of Adipogenesis, Annu. Rev. Cell Dev. Biol., 2000, pp. 145-171.

Steppan, et al., Resistin and obesity-associated insulin resistance, Trends in Endocrinology & Metabolism, 2002, pp. 18-23.

Tontonoz, et al., mPPARr2: tissue-specific regulator of an adipocyte enhancer, Genes & Development, 1994, pp. 1224-1234.

Spiegelman, et al., Adipogenesis and Obesity: Rounding Out the Big Picture, Cell, 1996, pp. 377-389.

* cited by examiner

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial
<220> FEATURE:
<223> OTHER INFORMATION: PPARgamma forward primer

<400> SEQUENCE: 1
ttcagctctg ggatgacctt                                                   20

<210> SEQ ID NO 2
<211> LENGTH: 20
<212> TYPE: DNA
<213> ORGANISM: Artificial
<220> FEATURE:
<223> OTHER INFORMATION: PPARgamma reverse primer

<400> SEQUENCE: 2
cgaagttggt gggccagaat                                                   20

<210> SEQ ID NO 3
<211> LENGTH: 23
<212> TYPE: DNA
<213> ORGANISM: Artificial
<220> FEATURE:
<223> OTHER INFORMATION: C/EBPalpha forward primer

<400> SEQUENCE: 3
gtgtgcacgt ctatgctaaa cca                                               23

<210> SEQ ID NO 4
<211> LENGTH: 22
<212> TYPE: DNA
<213> ORGANISM: Artificial
<220> FEATURE:
<223> OTHER INFORMATION: C/EBPalpha reverse primer

<400> SEQUENCE: 4
gttagtgaag agtctcagtt tg                                                22

<210> SEQ ID NO 5
<211> LENGTH: 19
<212> TYPE: DNA
<213> ORGANISM: Artificial
<220> FEATURE:
<223> OTHER INFORMATION: ACC forward primer

<400> SEQUENCE: 5
```
gcgtcgggta gatccagtt                                                19

<210> SEQ ID NO 6
<211> LENGTH: 20
<212> TYPE: DNA
<213> ORGANISM: Artificial
<220> FEATURE:
<223> OTHER INFORMATION: ACC reverse primer

<400> SEQUENCE: 6
ctcagtgggg cttagctctg                                               20

<210> SEQ ID NO 7
<211> LENGTH: 20
<212> TYPE: DNA
<213> ORGANISM: Artificial
<220> FEATURE:
<223> OTHER INFORMATION: FAS forward primer

<400> SEQUENCE: 7
ttgctggcac tacagaatgc                                               20

<210> SEQ ID NO 8
<211> LENGTH: 20
<212> TYPE: DNA
<213> ORGANISM: Artificial
<220> FEATURE:
<223> OTHER INFORMATION: FAS reverse primer

<400> SEQUENCE: 8
aacagcctca gagcgacaat                                               20

<210> SEQ ID NO 9
<211> LENGTH: 20
<212> TYPE: DNA
<213> ORGANISM: Artificial
<220> FEATURE:
<223> OTHER INFORMATION: FAT forward primer

<400> SEQUENCE: 9
tagtagaacc gggccacgta                                               20

<210> SEQ ID NO 10
<211> LENGTH: 20
<212> TYPE: DNA
<213> ORGANISM: Artificial
<220> FEATURE:
<223> OTHER INFORMATION: FAT reverse primer

<400> SEQUENCE: 10
cagttccgat cacagcccat                                               20

<210> SEQ ID NO 11
<211> LENGTH: 20
<212> TYPE: DNA
<213> ORGANISM: Artificial
<220> FEATURE:
<223> OTHER INFORMATION: SCD1 forward primer

<400> SEQUENCE: 11
catcgcctgc tctacccttt                                               20

<210> SEQ ID NO 12
<211> LENGTH: 20
<212> TYPE: DNA

```
<213> ORGANISM: Artificial
<220> FEATURE:
<223> OTHER INFORMATION: SCD1 reverse primer

<400> SEQUENCE: 12
gaactgcgct tggaaacctg                                                    20
```

COMPOSITION FOR OBESITY TREATMENT COMPRISING LIQUID-PHASE PLASMA

TECHNICAL FIELD

The present invention relates to a composition for treating obesity, which includes liquid type plasma. More particularly, the present invention relates to a method of producing liquid type plasma for inhibiting the differentiation or proliferation of adipocytes, a pharmaceutical composition for preventing or treating obesity using liquid type plasma produced using the method, and a method of preventing or treating obesity using the liquid type plasma.

BACKGROUND ART

As mankind has developed into a rich society, obesity has become one of the most serious diseases, and thus the World Health Organization (WHO) has declared that obesity is a target of diseases to be treated. Obesity is a metabolic disorder caused by an imbalance between intake and consumption of calories, and is caused by hypertrophy or hyperplasia of adipocytes in the body morphologically. Obesity is not only the most common malnutrition disorder in western society, but also in Korea, the importance of the treatment and prevention of obesity is rapidly increasing due to the rapid increase in the frequency of obesity due to the improvement of diet and westernization of lifestyle, which result from economic advances. Obesity is an important factor that not only psychologically disturbs individuals, but also increases the risk of various adult diseases socially. Obesity is known to be directly associated with the increased prevalence of various adult diseases such as type 2 diabetes, hypertension, hyperlipidemia, cardiovascular disease, and the like (Cell 87:377, 1999), all obesity-associated diseases are referred to as metabolic syndrome or insulin resistance syndrome, and these have been found as causes of arteriosclerosis and cardiovascular diseases. From the fact that obesity increases the incidence rate of various metabolic diseases and actual weight loss significantly reduces the incidence rate of such diseases, it can be inferred that fat-rich adipocytes mediate this phenomenon.

In the past, adipose tissue was considered to be an energy storage organ that stores excessive energy in the form of a triacylglycerol and releases it when needed, but has recently been accepted as an important endocrine organ that regulates energy homeostasis by secreting various adipokines, such as adiponectin, leptin, resistin, and the like (Trends Endocrinol Metab 13:18, 2002). Therefore, understanding of the proliferation of adipocytes and substances secreted by adipocytes and verification of their in vivo regulatory mechanisms are considered to serve as a basis for understanding obesity and various diseases caused thereby and for developing an effective therapeutic agent, and accordingly, studies on the regulation of adipocyte differentiation have been actively conducted, and it is considered to be the main mechanism that an increased number of adipocytes in patients with obesity originates from differentiation from pre-adipocytes in the body. Research on the differentiation process of pre-adipocytes into adipocytes has been conducted using cells such as 3T3-L1, and various types of transcription factors, particularly transcription factors known to be involved in adipogenesis, CAAT enhancer binding proteins (C/EBPs), peroxisome proliferator activated receptors (PPARs), and adipocyte determination and differentiation dependent factor1/sterol response element binding proteins (ADD1/SREBPs) are known to be expressed according to time differences and regulate the process (Bart A Jessen et al., Gene, 299, pp 95-100, 2002; Darlington et al., J. Biol. Chem., 273, pp 30057-30060, 1998; Brun R. P et al., Curr. Opin. Cell. Biol., 8, pp 826-832, 1996). Upon stimulation of hormones such as isobutylmethylxanthin, dexamethasone and insulin (MDI), C/EBPβ and C/EBPδ are first transiently expressed and initiates differentiation into adipocytes (Reusch J. E et al., Mol. Cell. Biol., 20, pp 1008-1020, 2000). This in turn induces increased expression of C/EBPδ and PPARg (James M. N. et al., J. Nutr., 130, pp 3122S-3126S, 2000). PPARg is known to be an especially important transcription factor for adipocyte differentiation, forms a dimer with a retinoic acid X receptor protein, and then binds to peroxisome proliferator response elements (PPREs) present in the promoters of various adipocyte genes (Tontonoz P. E et al., Genes Dev., 8, pp 1224-1234, 1994; Hwang, C. S et al., Cell Dev. Biol., 13, pp 873-877). The interaction of PPARγ and C/EBP-α is very crucial for differentiation into mature adipocytes, these transcription factors and adipocyte regulators stimulate differentiation into adipocytes, and expression amounts of adipocyte-specific proteins such as adipocyte fatty acid-binding protein 2 (aP2) and lipid metabolism enzymes such as fatty acid synthase (Fas) are increased. Furthermore, ADD1/SREBPs play an important role in lipid metabolism, but are also involved in the differentiation process. The expression of ADD1/SREBP1c in immature adipocytes is believed to contribute to the activation of PPARγ (Rosen E. D. et al., Annu. Rev. Cell Dev. Biol., 16, pp 145-171, 2000; Osborn T. F., J. Biol. Chem., 275, pp 32379-32382, 2000). Only adipocytes that have undergone the differentiation process synthesize fatty acids and store triglycerides. Therefore, current research trends are focused on the search for substances capable of inhibiting the metabolic process of adipogenic differentiation as a method for preventing or treating obesity and lipid-related metabolic diseases. In other words, attempts have been made to treat obesity through the regulation of adipocytes based on the mechanism of obesity, and these attempts have been intended to inhibit fat synthesis, reduce fat content by promoting lipolysis and oxidation, and reduce the number of adipocytes by inhibiting adipogenic differentiation, and transcription factors, proteins and adipokines, which are known to mediate or regulate these processes, are the targets of the development of new anti-obesity drugs. Actually, the peroxisome proliferator-activated receptor (PPAR) family, which is an adipogenic differentiation transcription factor, and leptin and adiponectin, which are adipocyte-secreted substances, have been the targets of many new drug development.

Current methods of treating obesity include dietetic therapy, exercise, and behavioral therapy, as well as methods of correcting daily habits, drug therapy, and surgical treatment. Obesity therapeutic agents are broadly classified into appetite suppressants, energy consumption promoters, and fat absorption inhibitors, such as Xenical™ (Roche Pharmaceuticals, Switzerland), Reductil™ (Abbott, USA), and Exolise™ (Atopharma, France), and most obesity drugs are appetite suppressants that suppress appetite by regulating the neurotransmitters associated with the hypothalamus. However, conventional therapeutic agents have been reported to have side effects such as heart disease, respiratory diseases, neurological diseases, and the like and low persistence of their efficacy. In addition, surgery for removing fat, gastroplasty or stomach band implantation for limiting the amount of food that can be digested by the body, and the like have been performed as obesity surgery methods, but therapeutic effects are not satisfactory compared to the side effects, surgery costs, and the like. For the fundamental treatment of obesity, there is a need for a new concept of obesity treatment based on the mechanisms capable of inhibiting the differentiation of pre-adipocytes into adipocytes.

Therefore, the applicants of the present invention completed the present invention. The present invention relates to a composition for treating obesity, which includes liquid type plasma, and the liquid type plasma of the present invention has a significant effect of inhibiting adipogenic differentiation and reducing intracellular lipogenesis and has an effect superior to that of a case in which a subject is directly treated with plasma, and thus it is anticipated that the composition of the present invention will be greatly utilized in preventing and treating obesity.

DISCLOSURE

Technical Problem

The present invention has been made to address the above-described problems of the related art, and relates to a composition for treating obesity, which includes liquid type plasma.

Therefore, it is an object of the present invention is to provide a method of producing liquid type plasma for preventing or treating obesity, a pharmaceutical composition for preventing or treating obesity using liquid type plasma produced by the method, and a method of preventing or treating obesity using liquid type plasma produced by the method.

However, the technical problem to be solved by the present invention is not limited to the above-mentioned problems, and other problems not mentioned can be clearly understood by those skilled in the art from the following description.

Technical Solution

Hereinafter, various embodiments of the present invention will be described with reference to the accompanying drawings. In the following description, for the purposes of complete understanding of the present invention, various specific details, such as specific forms, compositions, and processes, and the like, will be provided. However, specific embodiments may be practiced without one or more of these specific details, or with other known methods and forms. In other examples, known processes and manufacturing techniques will not be described in detail in order to not unnecessarily obscure the present invention. Reference throughout the present specification to "one embodiment" or "embodiments" indicates that particular features, forms, compositions, or characteristics described in connection with embodiments are included in one or more embodiments of the present invention. Accordingly, conditions of "one embodiment" or "embodiments" described in various locations throughout the present specification do not indicate the same embodiment of the present invention. In addition, particular features, forms, compositions, or characteristics may be combined in any suitable manner in one or more embodiments.

In one embodiment of the present invention, the term "obesity" refers to a condition or disease in which fat accumulated in the body due to energy imbalance has a higher excess body fat level than a normal level. According to the World Health Organization (WHO), in the Asia-Pacific region, a value obtained by dividing his or her body weight by the square of the height (meter unit) is used for the diagnosis of obesity, wherein a value of 23 to less than 25 is defined as an at risk weight, a value of 25 or higher is defined as overweight, a value of 30 or higher is defined as obesity, a value of 40 or higher is defined as extreme obesity, and a value of 50 or higher is defined as ultra-extreme obesity. Obesity may be classified into endocrine obesity (caused by endocrine abnormalities or brain diseases), simple obesity (caused by excessive nutrition), proliferative obesity (obesity due to an increased number of adipocytes), non-large obesity (obesity due to an increase in the size of adipocytes), upper body obesity, lower body obesity, visceral obesity, subcutaneous fat-type obesity, and the like, and these are all within the scope of the present invention.

In one embodiment of the present invention, the term "non-thermal atmospheric pressure plasma" refers to an ionized gas that satisfies Debye shielding. This is considered to be another state of matter, which represents a fourth state, other than the three states of matter: gas, liquid, and solid. In the plasma according to the present invention, electrons and cations may be generated by excitation and ionization of a neutral gas through phase transition of the neutral gas into plasma by an external voltage, and a radical generated by excitation of a molecular gas may be present. A plasma generator may be any known plasma generator without limitation as long as it is capable of producing low-temperature atmospheric-pressure plasma in accordance with the purposes of the present invention, and a nitrogen gas is preferably used, but the present invention is not limited thereto.

In one embodiment of the present invention, the term "liquid type plasma (LTP)" refers to high-density, high-energy plasma generated in a liquid, and the LTP may be produced by being exposed to atmospheric-pressure room-temperature non-thermal plasma (NTP). The term "liquid type plasma" may be used interchangeably with the term "plasma-conditioned liquid material," and the term "liquid material" refers to any material in a liquid state without limitation, but the liquid material is preferably water, saline, buffer, or culture media, and culture media is most preferably used.

In one embodiment of the present invention, the term "culture media" refers to culture media capable of supporting the growth and survival of cells in vitro, and includes all media generally used in the art, which are suitable for use in culturing cells. Media and culture conditions may be selected depending on the type of cells. A basic medium used in culturing cells is preferably a cell culture minimum medium (CCMM), and generally includes a carbon source, a nitrogen source, and a trace element component. Examples of the basic medium for culturing cells include Dulbeco's Modified Eagle's Medium (DMEM), Minimal Essential Medium (MEM), Basal Medium Eagle (BME), RPMI1640, F-10, F-12 (Minimal Essential Medium), Glasgow's Minimal Essential Medium (GMEM), and Iscove's Modified Dulbecco's Medium, but the basic medium is not particularly limited as long as it is used for the maintenance, proliferation, or differentiation of cells.

In one embodiment of the present invention, the term "treatment" means all actions that improve or beneficially change the symptoms of obesity and obesity-associated diseases by using the liquid type plasma according to the present invention. Those of ordinary skill in the art to which the present invention pertains will be able to understand the accurate criteria of obesity with reference to data provided by the Korean Medical Association, and the like and determine the degrees of alleviation, improvement, and treatment.

In one embodiment of the present invention, the term "prevention" means all actions that inhibit or delay the onset of obesity or other obesity-related diseases by using the liquid type plasma according to the present invention. It will be obvious to those of ordinary skill in the art that the composition of the present invention having an effect of treating obesity is able to prevent these diseases by using the liquid type plasma of the present invention before initial symptoms or symptoms of obesity occur.

As used herein, the term "pharmaceutical composition" refers to a composition to be administered for a specific purpose. For the purpose of the present invention, the pharmaceutical composition of the present invention includes, as an active ingredient, liquid type plasma produced by treating liquid material with plasma, and may include a protein involved therein and a pharmaceutically acceptable carrier, an excipient or a diluent. The term "pharmaceutically acceptable" carrier or excipient means a carrier or excipient approved by the government regulatory department, or listed in the pharmacopoeia approved by the government or other generally approved pharmacopoeia, for use in vertebrates, more particularly, humans.

For parenteral administration, the pharmaceutical compositions of the present invention may be in the form of a suspension, solution or emulsion in an oily or aqueous carrier and may be produced in the form of a solid or semi-solid. In addition, the pharmaceutical composition of the present invention may include a formulating agent such as a suspending agent, a stabilizing agent, a solubilizing agent, and/or a dispersing agent, and may be sterilized. The pharmaceutical composition may be stable under preparation and storage conditions and may be preserved against the contaminating action of microorganisms such as bacteria or fungi. Alternatively, the pharmaceutical composition of the invention may be in a sterile powder form for reconstitution with a suitable carrier before use. The pharmaceutical composition may be present, as a unit-dose form, in micro needle patches or ampoules, in other unit-dose containers, or in multi-dose containers. Alternatively, the pharmaceutical composition may be stored under a freeze-dried (lyophilized) condition requiring only the addition of a sterile liquid carrier, e.g., water for injection immediately before use. Immediately, an injection solution and a suspension may be prepared into the form of sterile powder, granules, or tablets.

In some non-limiting embodiments, the pharmaceutical composition of the present invention may be formulated, or may be included in the form of microspheres in a liquid. In certain non-limiting embodiments, the pharmaceutical composition of the present invention may include a pharmaceutically acceptable compound and/or a mixture thereof at a concentration between 0.001 U/kg and 100,000 U/kg. In addition, in certain non-limiting embodiments, the pharmaceutical composition of the present invention may include suitable excipients such as a preservative, a suspending agent, an additional stabilizing agent, a dye, a buffer, an antimicrobial agent, an antifungal agent, and an isotonic agent, e.g., sugar or sodium chloride. As used herein, the term "stabilizing agent" refers to a compound that is optionally used in the pharmaceutical composition of the present invention to increase shelf life. In non-limiting embodiments, the stabilizing agent may be a sugar, an amino acid, or a polymer. In addition, the pharmaceutical composition of the present invention may include one or more pharmaceutically acceptable carriers, and the carriers may be solvents or dispersion media. Non-limiting examples of pharmaceutically acceptable carriers include water, saline, ethanol, polyols (e.g., glycerol, propylene glycol and liquid polyethylene glycol), oils, and suitable mixtures thereof. Non-limiting examples of sterilization techniques applied to the pharmaceutical composition of the present invention include filtration through a bacteria-inhibiting filter, terminal sterilization, incorporation of sterile preparations, treatment, gas treatment sterilization, heating, vacuum drying, and lyophilization.

As used herein, the term "administration" means introduction of the composition of the present invention to a patient in any suitable manner, and the composition of the present invention may be administered through any general route as long as it enables the composition to reach target tissue therethrough. The composition of the present invention may be administered via routes such as oral administration, intraperitoneal administration, intravenous administration, intramuscular administration, subcutaneous administration, intradermal administration, intranasal administration, intrapulmonary administration, intrarectal administration, intraperitoneal administration, and intrathecal administration. The treatment method of the present invention may include administering the pharmaceutical composition in a pharmaceutically effective amount. In the present invention, the effective amount may be adjusted depending on various factors including the type of disease, the severity of disease, the types and amounts of the active ingredient included in the composition and other ingredients, the type of preparation, the age and body weight of a patient, general health conditions, gender and diet, administration time, administration routes, an excretion rate of the composition, treatment periods, and simultaneously used drugs.

According to an embodiment of the present invention, there is provided a method of producing liquid type plasma for inhibiting adipogenic differentiation, the method including: (a) filling a plasma generator with a carrier gas; (b) supplying a voltage of 1 kV to 20 kV and a frequency of 10 kHz to 30 kHz to the plasma generator to generate plasma; and (c) treating liquid material with the generated plasma, wherein, in process (a), the carrier gas includes any one or more selected from the group consisting of nitrogen, helium, argon, and oxygen, the carrier gas is a mixture of helium and oxygen in a volume (vol %) ratio of 20:80, the treatment of process (c) is performed at a distance of 0.1 cm to 15 cm from a surface of the liquid material for 1 minute per 1 ml, and the liquid material of process (c) is water, saline, a buffer, or a medium.

According to another embodiment of the present invention, there is provided a composition for inhibiting adipogenic differentiation, which includes liquid type plasma produced using any one or more of the above-described methods.

According to another embodiment of the present invention, there is provided a pharmaceutical composition for preventing or treating obesity, which includes the composition for inhibiting adipogenic differentiation as an active ingredient, wherein the pharmaceutical composition is in the form of an oral preparation, a parenteral preparation, or a local preparation, and the pharmaceutical composition is used alone or in combination with surgery, radiotherapy, hormone treatment, chemotherapy, and methods using a biological response modifier.

According to another embodiment of the present invention, there is provided a method of preventing or treating obesity, which includes administering a pharmaceutical composition prepared using any one or more of the above-described methods to an individual.

According to another embodiment of the present invention, there is provided a use of a pharmaceutical composition prepared using any one or more of the above-described methods for preventing or treating obesity.

Hereinafter, the present invention will be described in detail step by step.

Advantageous Effects

The present invention relates to a composition for treating obesity, which includes liquid type plasma, and the liquid type plasma of the present invention has a significant effect of inhibiting adipogenic differentiation and reducing intracellular lipogenesis and has an effect superior to that in a case in which a subject is directly treated with plasma, and thus it is anticipated that the composition of the present invention will be greatly utilized in the prevention and treatment of obesity.

BEST MODE

To confirm the effect of liquid type plasma on lipogenesis, intracellular lipid accumulation was monitored by Oil Red O staining and analysis of triglyceride contents.

As experimental results, it was confirmed that, while the intensity of Oil Red O staining and triglyceride contents were gradually increased in cells of a control, adipogenic differentiation was significantly inhibited in 3T3-L1 cells treated with liquid type plasma for 4 days. In particular, liquid type plasma significantly reduced oil formation in differentiated cells as compared to the control (67%±3%). It was also confirmed that, in analysis of triglyceride (TG) contents, adipogenic differentiation was significantly inhibited by 23±2% in liquid type plasma-treated cells, as compared to control cells not treated with liquid type plasma. These results indicate that liquid type plasma treatment may dramatically inhibit adipogenic differentiation of 3T3-L1 cells.

[Mode of the Invention]

Hereinafter, the present invention will be described in further detail with reference to the following examples. It will be obvious to those of ordinary skill in the art that these examples are provided only to more particularly describe the present invention and are not intended to limit the scope of the present invention in accordance with the essence of the present invention.

Example 1. Confirmation of Effect of Non-Thermal Plasma Treated Solution (NTP) on Obesity Treatment Example 1-1. Preparation of Non-Thermal Plasma Treated Solution (NTP)

Figure 1:
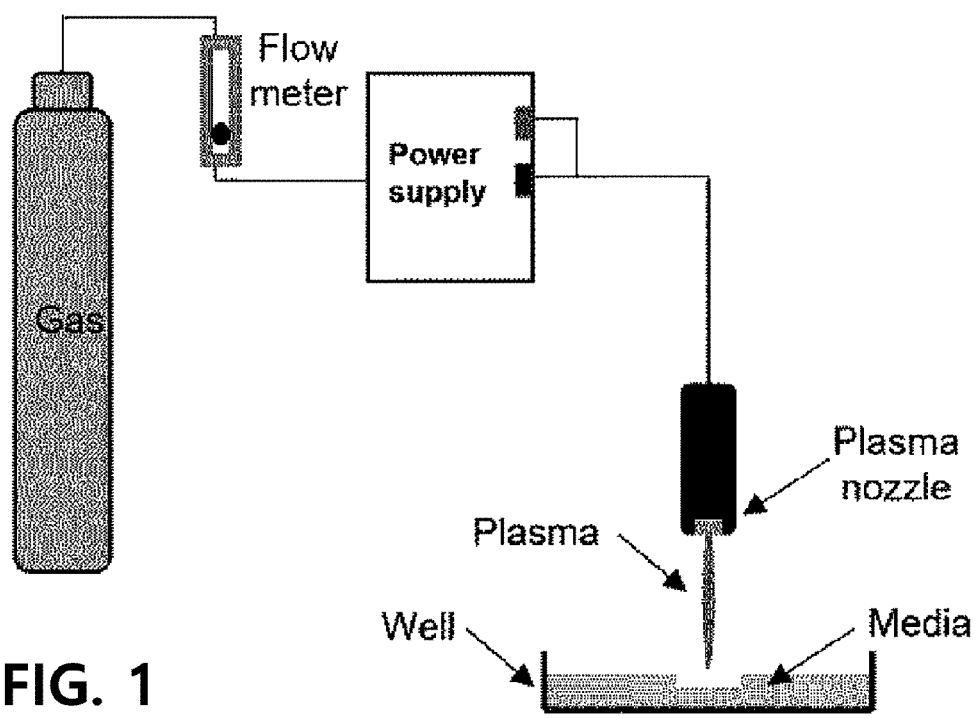
FIG. 1 is a view illustrating the production of liquid type plasma according to an embodiment of the present invention.
Figure 2A:
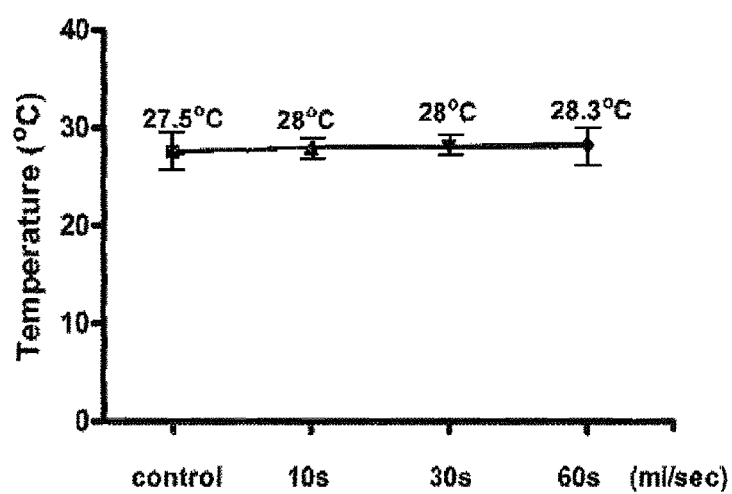
FIGS. 2A and 2B are graphs showing changes in temperature and acidity (pH) of media according to plasma treatment time, according to an embodiment of the present invention.
Figure 2B:
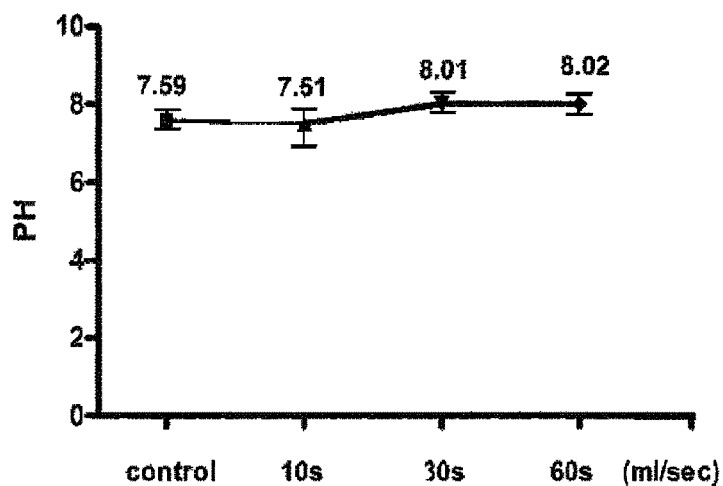

A non-thermal plasma treated solution (NTP) was prepared, using a plasma device including a pair of high-voltage and ground electrodes ($Al_2O_3$, 10×40 $mm^2$, a gap of 2 mm between the electrodes) separated from plasma by a ceramic barrier, i.e., not in direct contact with plasma, by treating a culture dish (100 mm, TPP, Renner, Dannstadt, Germany) in which 10 ml of cell media was dispensed, with plasma for 1 minute per 1 ml at a distance of 4 cm from a surface of the bottom of the culture dish, by supplying, as a carrier gas, a mixture of helium and oxygen in a ratio of 20:80 at a flow rate of 10 L/min. At this time, power supply specifications of the plasma device may be a voltage of a minimum of 2 kV and a maximum of 13 kV and an average frequency of 20 kHz to 30 kHz, and a voltage of 4 kV is most preferably used. The preparation of the non-thermal plasma treated solution is illustrated in FIG. 1, and changes in temperature and acidity (pH) of media according to plasma treatment time are illustrated in FIGS. 2A and 2B. As a result of the experiment, the temperature of media upon treatment with plasma for 1 minute was changed from 27.5° C. to 28.3° C., and acidity was changed from 7.59 to 8.02.

Example 1-2. Confirmation of Cytotoxicity of NTP Against 3T3-L1 Cells

It was examined whether the NTP exhibits cytotoxicity against adipocytes. 3T3-L1 pre-adipocytes were obtained from a U.S. cell line bank (ATCC, Manassas, Va., USA), and cultured using a method of thawing the cells with a DMEM (GIBCO, Carlsbad, Calif., USA) growth medium (GM) supplemented with 10% serum and antibiotics under 5% $CO_2$ and humidified conditions, and replacing, on day 2 after thawing, the medium with a differentiation medium (DM) containing 0.5 mM 3-isobutyl-1-methylxanthine (IBMX, Sigma Aldrich, St. Louis, Mo., USA), 1 mM dexamethasone, 10% FBS, and 10 mg/ml of insulin, and then replacing the medium every three days.

Figure 3:
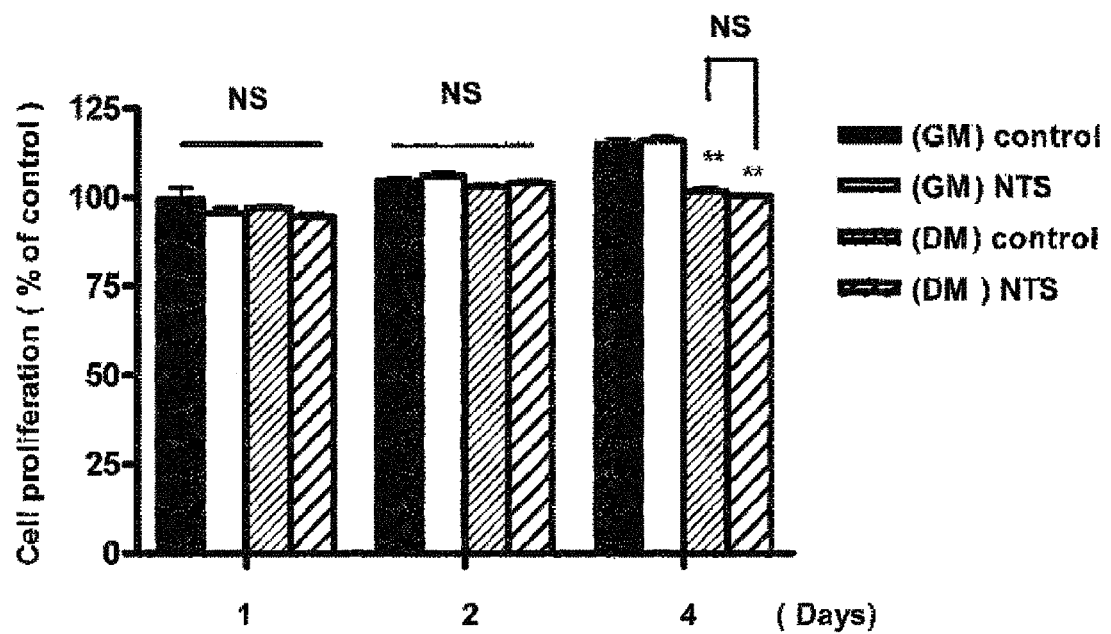
FIG. 3 is a graph showing cytotoxicity experimental results upon treatment of 3T3-L1 pre-adipocytes with liquid type plasma, according to an embodiment of the present invention.

Apoptotic cell death analysis was performed using 3-(4,5-dimethylthiazol-2-yl)-2,5-diphenyltetrazolium bromide (MTT, Sigma-Aldrich, St Louis, Mo., USA). Briefly, 3T3-L1 pre-adipocytes were inoculated into a 96-well cell culture plate, and after differentiation was induced, the cells were treated with the NTP or a vehicle. Cell viability results were converted as normalized percentage on the basis of non-treated cells, and the results thereof are shown in FIG. 3. The experimental results showed that the NTP had no cytotoxicity against the 3T3-L1 cells.

Figure 4:
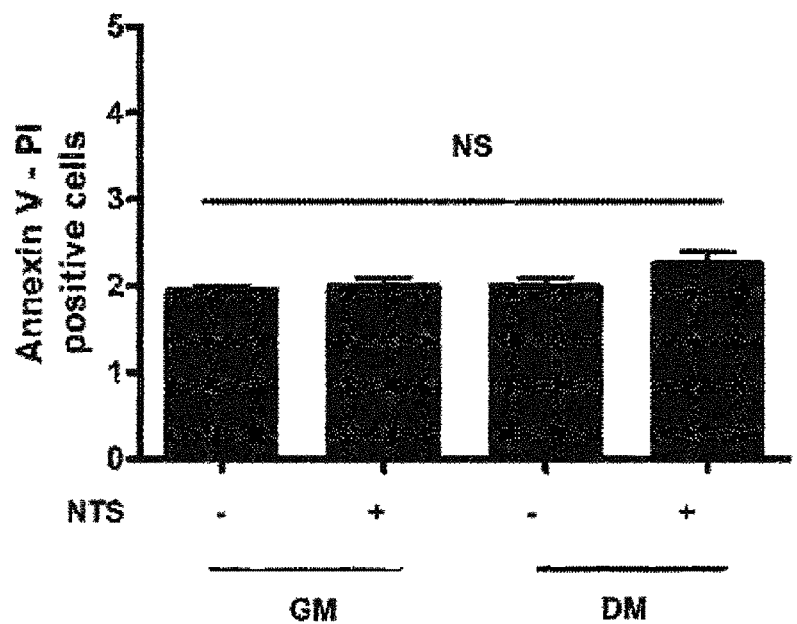
FIG. 4 is a graph showing annexin V-PI staining results upon treatment of 3T3-L1 pre-adipocytes with liquid type plasma, according to an embodiment of the present invention.
Figure 5:
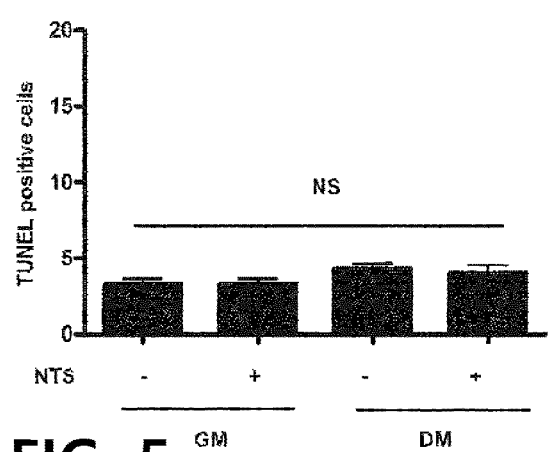
FIG. 5 is a graph showing TUNEL assay results upon treatment of 3T3-L1 pre-adipocytes with liquid type plasma, according to an embodiment of the present invention.

In addition, it was examined whether or not there was cytotoxicity through annexin V-PI staining (early cell death marker) and a TUNEL assay (late cell death marker). The annexin V-PI staining was performed using an Annexin V-FITC/PI cell death detection kit (BD Biosciences, Bedford, Mass., USA) in accordance with the manufacturer's recommended protocol, and measured using a BD FACS AriaIII instrument (BD Biosciences) at excitation and emission wavelengths of 488 nm and 530 nm. The TUNEL assay was performed by treating cells grown on coverslips with the NTP or a vehicle for 24 hours, fixing the cells with 4% paraformaldehyde at room temperature for 1 hour, and then performing DNA fragment analysis thereon using a cell death detection kit (Roche Molecular Biochemicals) in accordance with the manufacturer's instructions. The stained cells were quantitatively counted using a fluorescence microscope (Carl Zeiss, Oberkochen, Germany). The results thereof are illustrated in FIGS. 4 and 5, respectively. The experimental results showed that the NTP treatment did not induce cell death of the 3T3-L1 cells.

Figure 6:
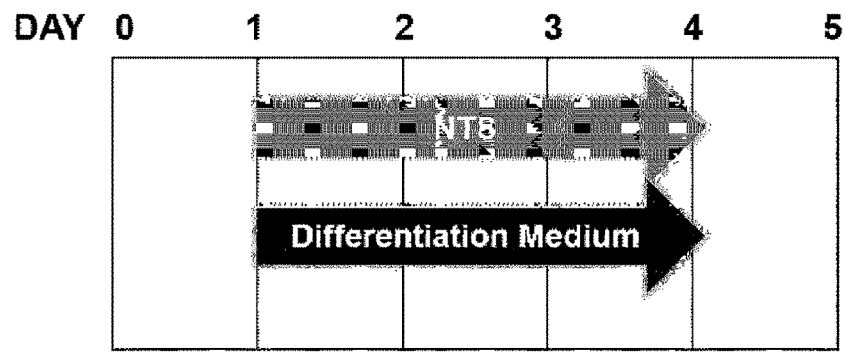
FIG. 6 is a view illustrating a time frame for liquid type plasma treatment in order to confirm an effect of liquid type plasma on adipogenic differentiation, according to an embodiment of the present invention.
Figure 7A:
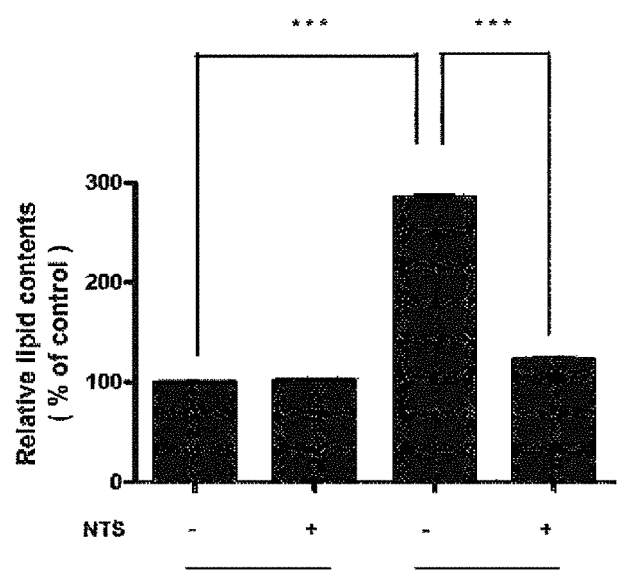
FIGS. 7A and 7B are graphs showing results of analyzing lipid and triglyceride contents upon treatment of 3T3-L1 pre-adipocytes with liquid type plasma, according to an embodiment of the present invention.
Figure 7B:
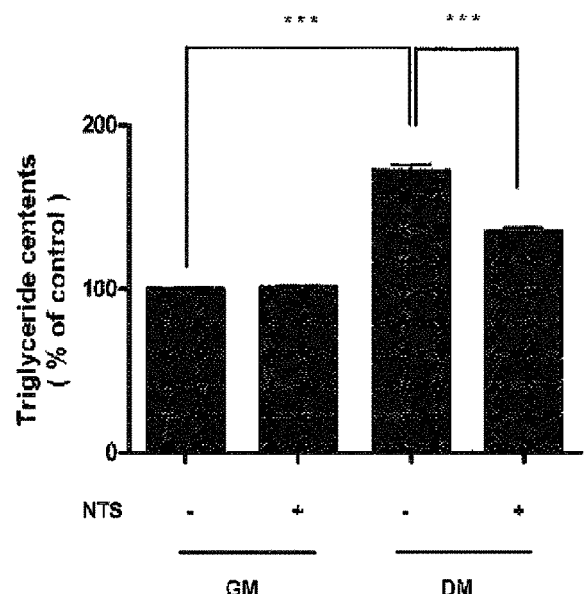
Figure 8A:
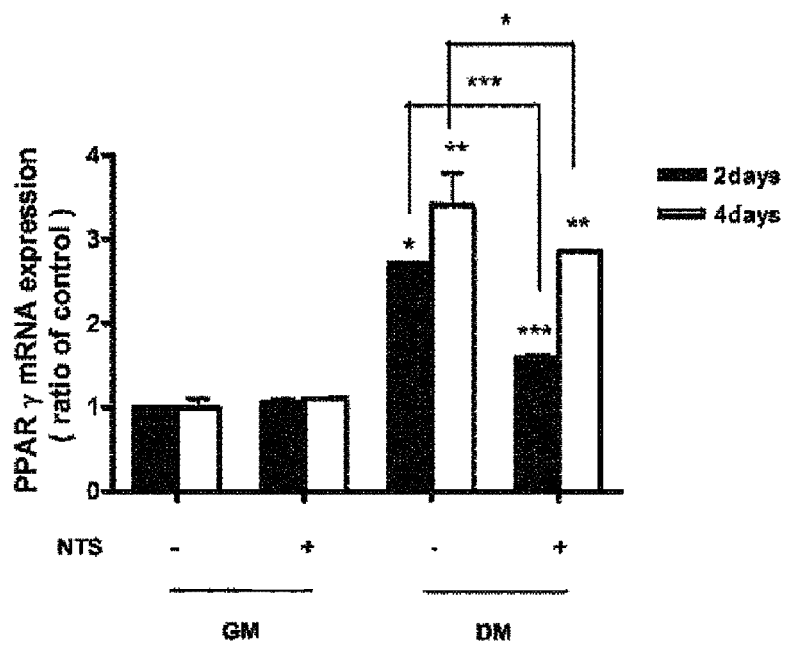
FIGS. 8A to 8F are graphs showing results of inhibiting the gene expression of lipogenic factors upon treatment of 3T3-L1 pre-adipocytes with liquid type plasma, according to an embodiment of the present invention.
Figure 8B:
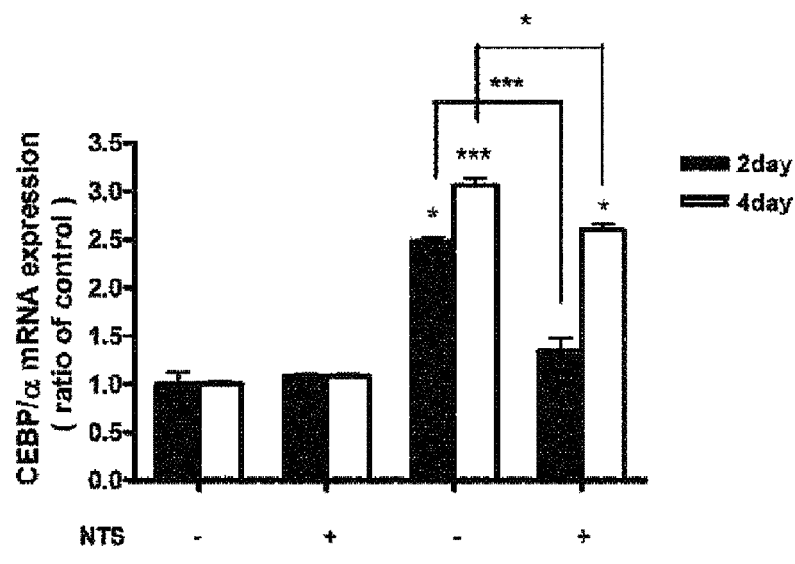
Figure 8C:
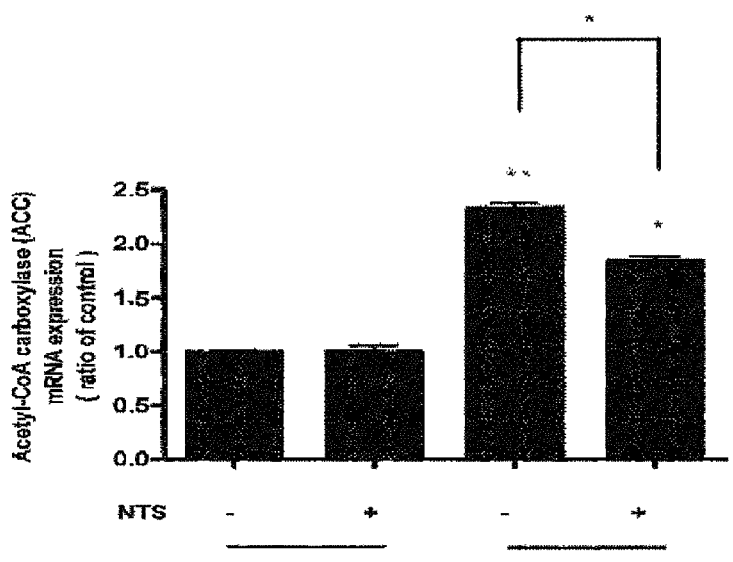
Figure 8D:
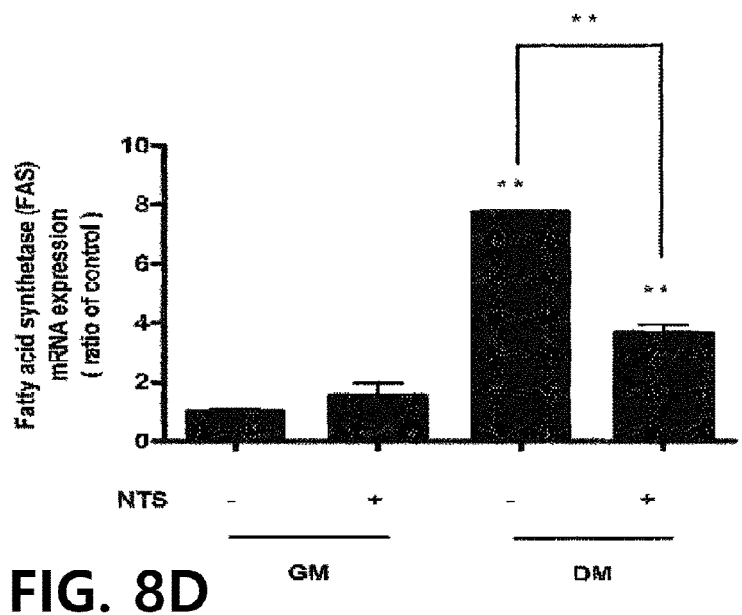
Figure 8E:
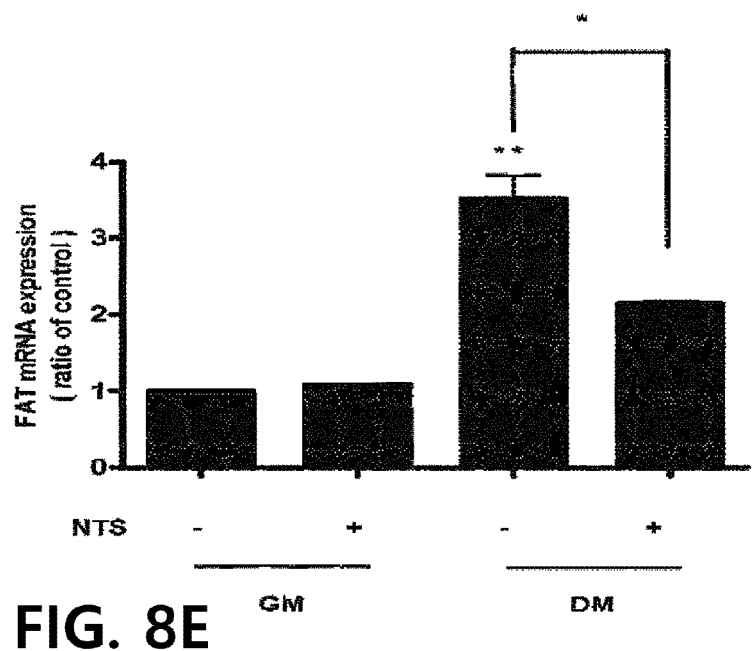
Figure 8F:
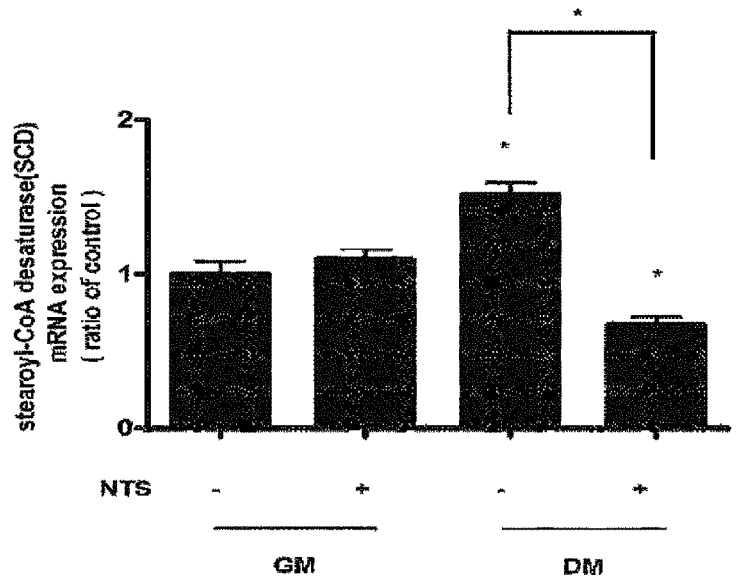

Example 1-3. Confirmation of Effect of NTP on Inhibiting Adipogenic Differentiation in 3T3-L1 Cells To confirm the effect of NTP on lipogenesis, intracellular lipid accumulation was monitored by Oil Red O staining and triglyceride content analysis. A time frame for the NTP treatment is illustrated in FIG. 6. The Oil Red O staining was carried out by washing the cells with PBS, fixing the cells with 10% formalin, and immersing the cells in a 60% Oil Red O solution (Sigma Aldrich, St. Louis, Mo., USA) at room temperature for 20 minutes. The stained cells were washed with distilled water and photographed using an EVOS FL automated cell imaging system (Thermo Fisher Scientific, Waltham, Mass., USA), and after photographing, an Oil Red O dye was dissolved in 100% isopropanol, and absorbance at a wavelength of 520 nm was measured using an ELISA reader (Bio-Tek, Winooski, Vt., USA). The triglyceride content analysis was performed using a triglyceride colorimetric assay kit (Cayman, Ann Arbor, Mich., USA). Specifically, the cells were washed three times with PBST (1% Triton X-100 in PBS, pH 7.4), sonicated for 5 minutes to homogenize the cell suspension, and the cell lysate was analyzed according to the manufacturer's instructions to measure triglyceride contents by measuring absorbance. The Oil Red O staining and triglyceride content analysis results are illustrated in FIGS. 7A and 7B. As a result of the experiment, it was confirmed that, while the intensity of Oil Red O staining and triglyceride contents were gradually increased in the cells of a control, adipogenic differentiation was significantly inhibited in 3T3-L1 cells treated with the NTP for 4 days. In particular, the NTP significantly reduced oil formation in differentiated cells as compared to the control (67%±3%). It was also confirmed that, in analysis of triglyceride (TG) contents, adipogenic differentiation was significantly inhibited by 23±2% in NTP-treated cells, as compared to control cells not treated with the NTP. These results indicate that the NTP treatment may dramatically inhibit adipogenic differentiation of 3T3-L1 cells.

Example 1-4. Confirmation of Effect of NTP on Inhibiting Expression of Lipogenic Factors in 3T3-L1 Cells To confirm the effect of NTP on inhibiting the expression of lipogenic factors in 3T3-L1 cells, the expression levels of PPARγ, C/EBPα, Acetyl-CoA carboxylase (ACC), fatty acid synthase (FAS), FAT, and SCD1 were confirmed by qPCR. PPARγ and C/EBPα, which are lipogenic transcription factors, are well known for regulating adipogenic differentiation. To this end, total RNA was extracted from the 3T3-L1 cells using a TRIzol® reagent (Gibco-BRL, Grand Island, N.Y., USA), and for cDNA synthesis, 1 μg of RNA and 10 μl of ReverTrace qPCR RT (Toyobo Co., Osaka, Japan), and the target genes were quantified by first-step real time PCR using Lightcycler 96 (Roche Molecular Biochemicals, Basel, Switzerland). The sequences of primers used in the qPCR are shown in Table 1, and the qPCR results are shown in FIGS. 8A to 8F.

TABLE 1

| | | |
|---|---|---|
| PPARγ | Forward | 5'-TTCAGCTCTGGGATGACCTT-3' |
| | Reverse | 5'-CGAAGTTGGTGGGCCAGAAT-3' |
| C/EBPα | Forward | 5'-GTGTGCACGTCTATGCTAAACCA-3' |
| | Reverse | 5'-GTTAGTGAAGAGTCTCAGTTTG-3' |
| ACC | Forward | 5'-GCGTCGGGTAGATCCAGTT-3' |
| | Reverse | 5'-CTCAGTGGGGCTT AGCTCTG-3' |
| FAS | Forward | 5'-TTGCTGGCACTACAGAATGC-3' |
| | Reverse | 5'-AACAGCCTCAGAGCGACAAT-3' |
| FAT | Forward | 5'-TAGTAGAACCGGGCCACGTA-3' |
| | Reverse | 5'-CAGTTCCGATCACAGCCCAT-3' |
| SCD1 | Forward | 5'-CATCGCCTGCTCTACCCTTT-3' |
| | Reverse | 5'-GAACTGCGCTTGGAAACCTG-3' |

Figure 9A:
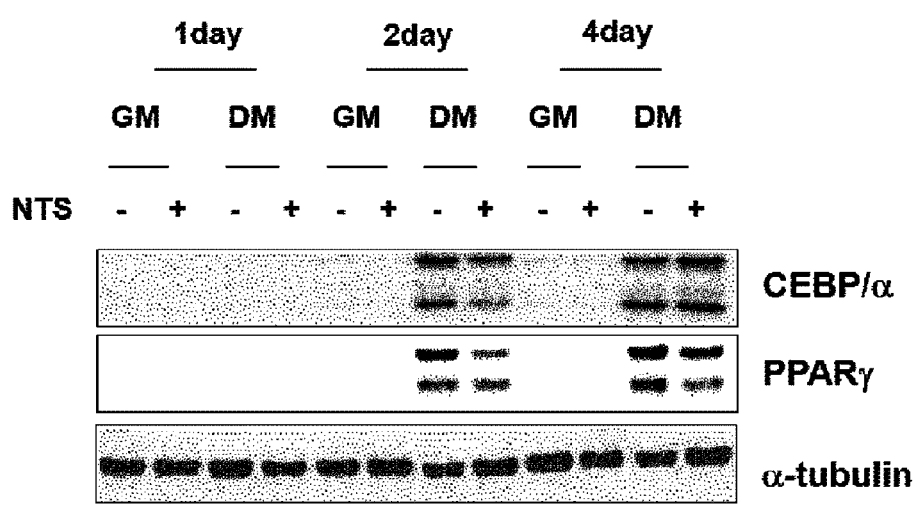
FIGS. 9A and 9B are graphs showing results of inhibiting the protein expression of lipogenic factors upon treatment of 3T3-L1 pre-adipocytes with liquid type plasma, according to an embodiment of the present invention.
Figure 9B:
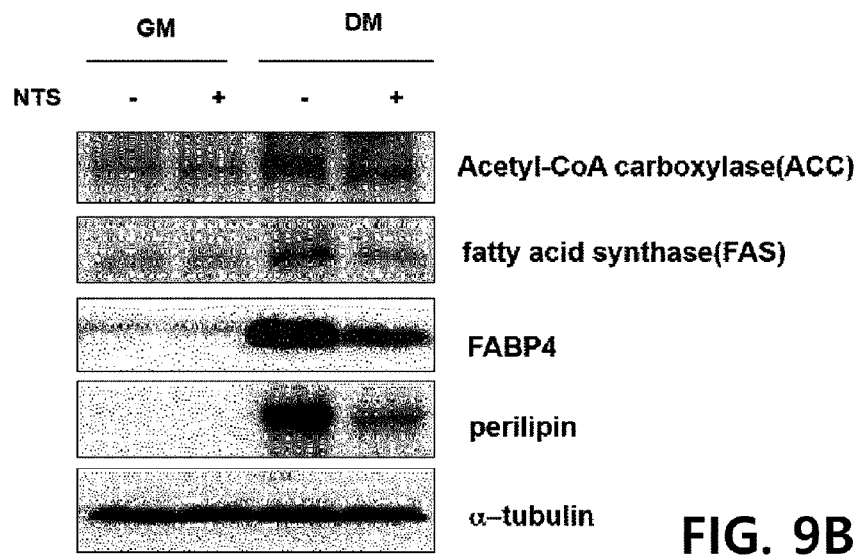

In addition, to examine whether NTP treatment inhibits adipogenic differentiation at a protein level, western blotting was performed. As primary antibodies, PPARγ, C/EBPα, CHOP, BIP, PERK, p-PERK, p-eIF2α, eIF2α, p-IRE1α, IRE1α, FABP4, perilipin, and α-tubulin antibodies (1:1000, Cell Signaling Technology, Danvers, Mass., USA) were used, and anti-rabbit IgG or anti-mouse IgG antibodies (1:2000, Cell Signaling Technology, Danvers, Mass., USA) were used as secondary antibodies. Immune response detection was performed using an ECL western blotting kit (GE, Hercules, Calif., USA) according to the manufacturer's instructions. The results thereof are illustrated in FIGS. 9A and 9B.

Lastly, immunofluorescent staining of PPARγ and perilipin was performed. Specifically, 3T3-L1 cells were cultured on coverslips (Thermo Fisher Scientific, Rochester, N.Y., USA), differentiated and treated with the NTP (1 minute/ml) or a vehicle (control). 24 hours after culturing, the cells were fixed with 4% formaldehyde and blocked with 5% BSA (Millipore, Bedford, Mass., USA) in PBS for 5 hours, and the cells were reacted with polyclonal rabbit PPARγ or perilipin antibodies (1:100, Cell Signaling, USA) for 2 hours, washed with PBS, and then treated with Alexa 546- and Alexa 488-conjugated antibodies (1:500, Molecular Probe, Eugene, Oreg., Calif., USA) for 1 hour. Nuclei were stained with Hoechst 33258 (Molecular Probe) at room temperature for 15 minutes. Fluorescent stained images were acquired using a fluorescence microscope (EVOS FL Auto, Thermo Fisher Scientific, Waltham, Mass., USA).

Interestingly, the experimental results showed that NTP treatment significantly reduced mRNA levels of PPARγ and C/EBPα in 3T3-L1 cells on day 2 and day 4. However, such decreases were not shown in the growth media group. These results suggest that the NTP treatment may inhibit lipogenesis at a gene transcription level. Consistent with the gene expression patterns, when cells were cultured in lipogenic media, lipid synthesis-related proteins (PPARγ, C/EBPα, perilipin, acetyl CoA carboxylase, fatty acid synthesis, and FABP4) were gradually induced. It was confirmed that the NTP treatment inhibited the expression of PPARγ and C/EBPα on day 2, but the expression of C/EBPα was not inhibited by the NTP on day 4. In addition, immunofluorescence staining results showed that PPARγ was clearly localized in the nuclei of the differentiated 3T3-L1 adipocytes, rather than pre-adipocytes. The mRNA levels of lipogenesis-related genes including ACC, FAS, FAT, and SCD1 were significantly reduced in the NTP-treated group. Consistent with the mRNA expression patterns, ACC and FAS protein levels were also significantly reduced by the NTP treatment. Perilipins and FABP4 are known to play an important role in the formation of intracellular lipid droplets. From the results of the present invention, it was confirmed that the NTP treatment significantly reduced protein levels of perilipins and FABP4. From the immunofluorescence staining results of perilipins, it was confirmed that the staining of lipid droplets of perilipins was significantly reduced in the NTP-treated group as compared to the group not treated with the NTP. These results indicate that the NTP treatment may dramatically inhibit the expression of lipogenesis-related genes and lipogenesis properties.

Figure 10:
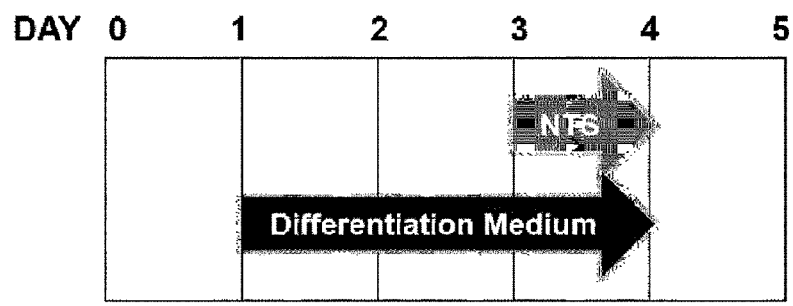
FIG. 10 is a view illustrating a time frame for liquid type plasma treatment in order to confirm whether liquid type plasma had an inhibitory effect in a later stage of adipogenic differentiation, according to an embodiment of the present invention.

Example 1-5. Confirmation of Effect of NTP on Inhibiting Late Adipogenic Differentiation in 3T3-L1 Cells To examine whether the NTP has an effect of inhibiting late adipogenic differentiation, the cells were treated with the NTP on day 4 of cell differentiation, and then lipid accumulation and the expression of lipogenesis-related genes were examined on day 5. A time frame for the NTP treatment is illustrated in FIG. 10. The mRNA and protein expression levels were confirmed using the same method as that used in Example 1-4.

Figure 11A:
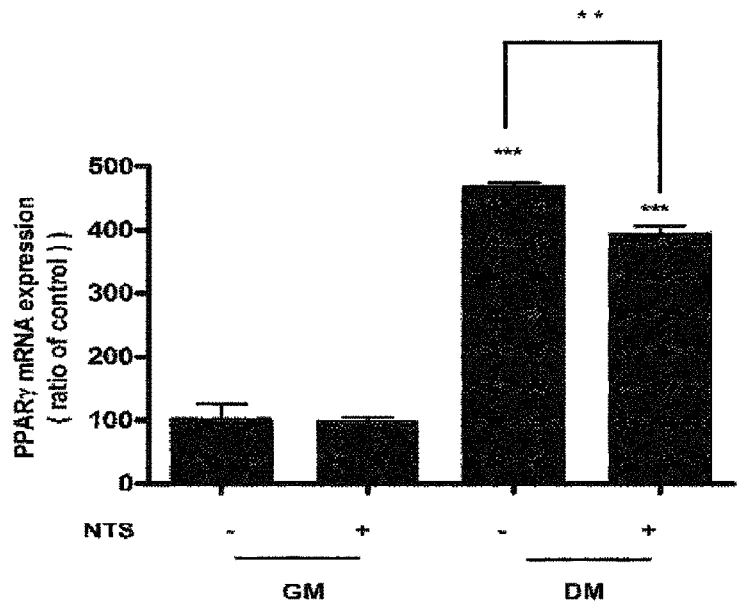
FIGS. 11A and 11B are graphs showing results of confirming an effect of liquid type plasma treatment on inhibiting late adipogenic differentiation by measuring mRNA expression levels, wherein 3T3-Li-differentiated adipocytes were treated with liquid type plasma, according to an embodiment of the present invention.
Figure 11B:
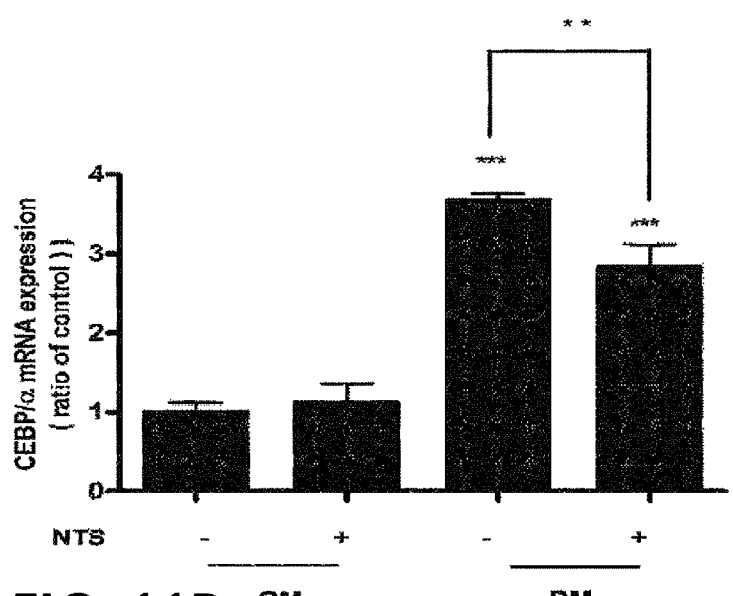

As a result of measuring the mRNA levels of PPARγ and C/EBPα in the NTP-treated cells, it was confirmed that the mRNA expression levels of PPARγ and C/EBPα were significantly reduced by the NTP treatment, but this case exhibited an insignificant effect as compared to the case of NTP treatment at the initial expression stage. The results thereof are shown in FIGS. 11A and 11B.

Figure 12A:
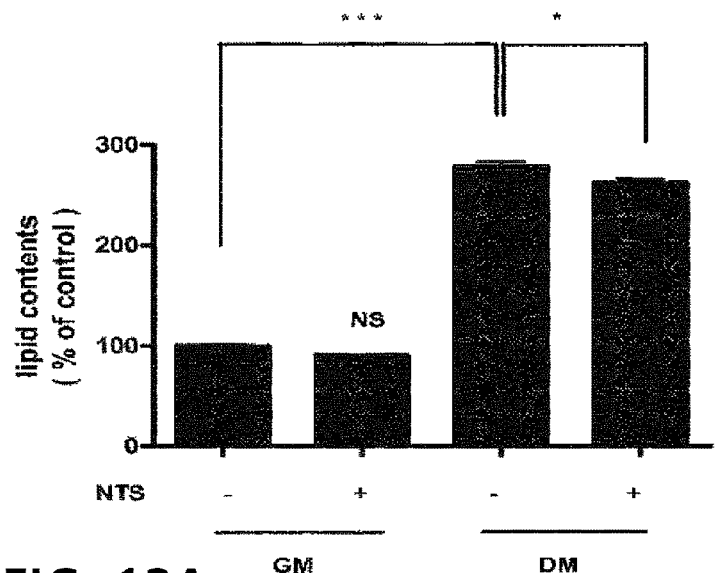
FIGS. 12A and 12B are graphs showing results of confirming an effect of liquid type plasma treatment on inhibiting late adipogenic differentiation through Oil Red O staining and analysis of triglyceride (TG) contents, wherein 3T3-Li-differentiated adipocytes were treated with liquid type plasma, according to an embodiment of the present invention.
Figure 12B:
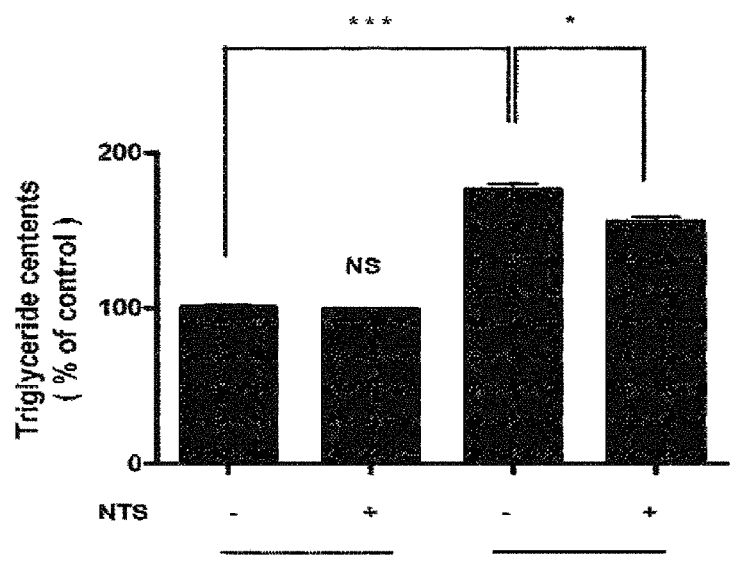

In addition, as a result of examining intracellular lipid accumulation through Oil Red O staining and analysis of triglyceride (TG) contents, it was confirmed that lipid accumulation was also significantly reduced in the NTP-treated cells. In particular, the NTP treatment reduced TG contents by 89%. The results thereof are shown in FIGS. 12A and 12B.

Figure 13:
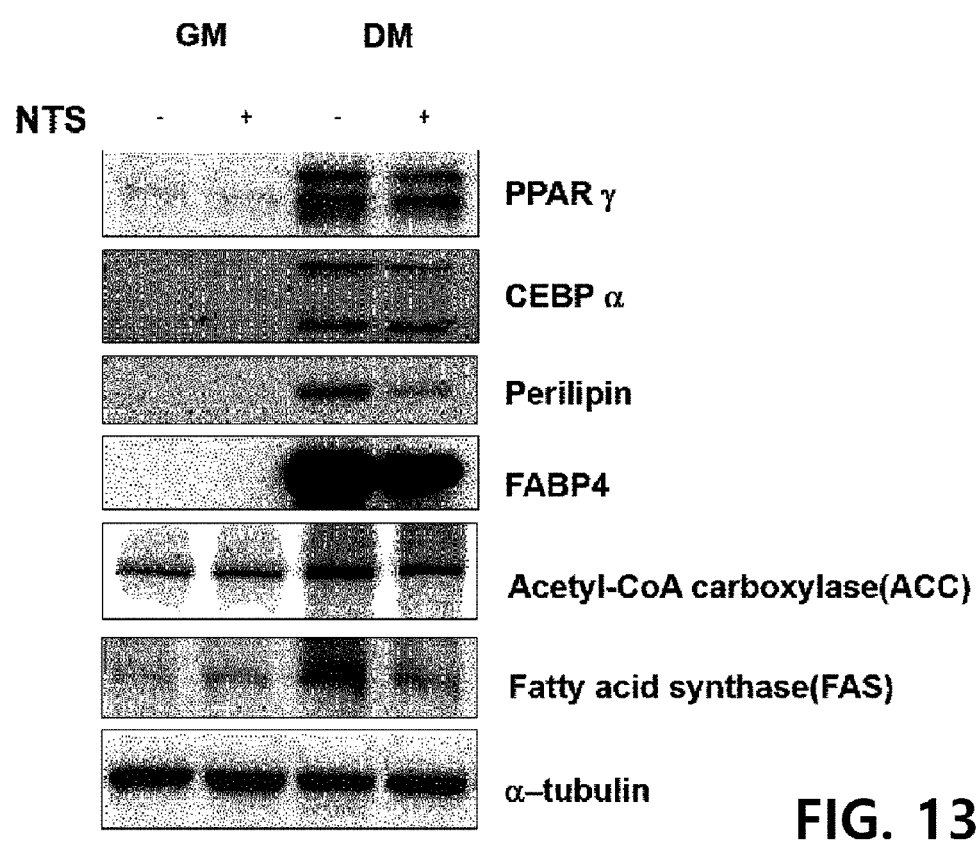
FIG. 13 is a graph showing results of confirming an effect of liquid type plasma treatment on inhibiting late adipogenic differentiation by measuring protein expression levels, wherein 3T3-Li-differentiated adipocytes were treated with liquid type plasma, according to an embodiment of the present invention.

It was also confirmed that the protein levels of adipocyte-specific markers including PPARγ, C/EBPα, ACC, FAS, perilipin, and FABP4 were significantly reduced in the NTP-treated cells. The results thereof are shown in FIG. 13. These results suggest that the NTP has a significant effect of inhibiting early lipogenesis and late lipogenesis in 3T3-L1 differentiation.

Figure 14:
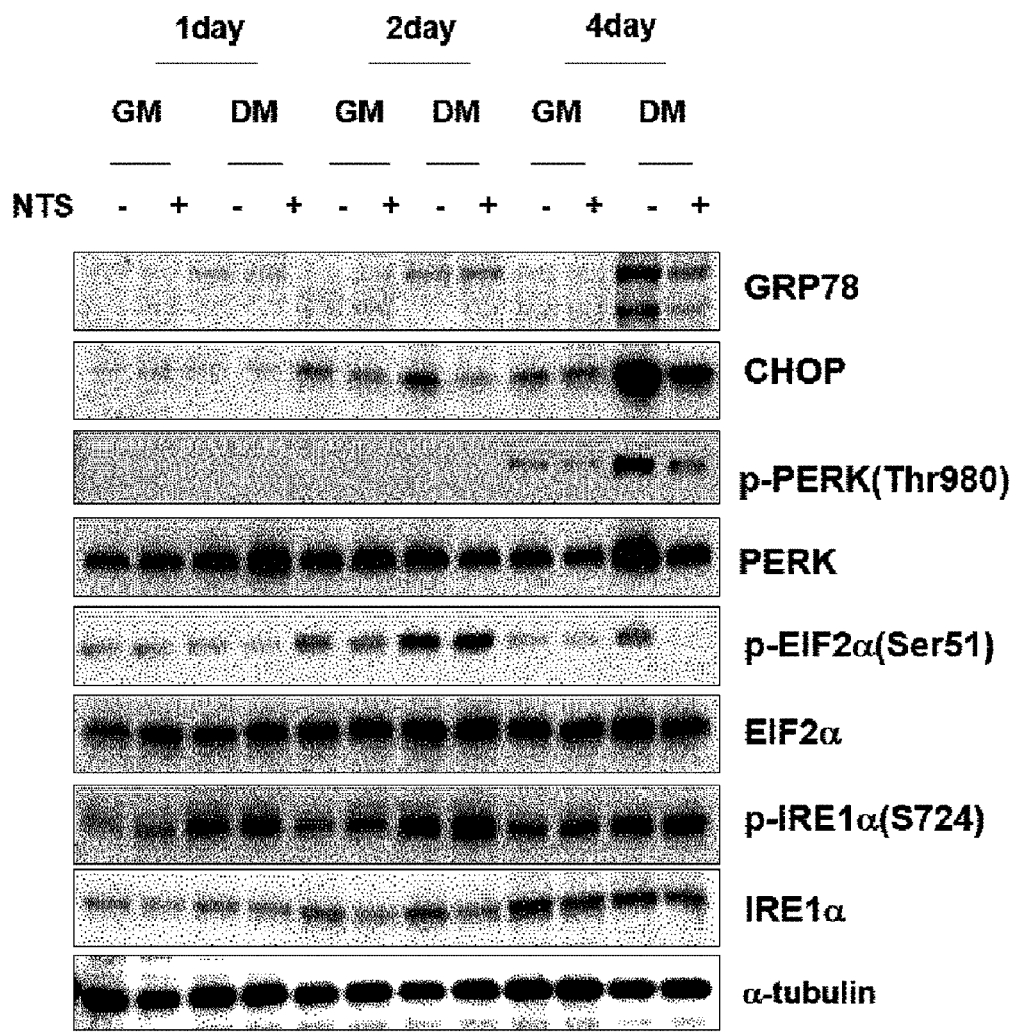
FIG. 14 is a graph showing results of confirming the degrees of ER stress and UPR activation by measuring protein expression levels upon treatment of 3T3-L1 pre-adipocytes with liquid type plasma, according to an embodiment of the present invention.

Example 1-6. Confirmation of Effect of NTP on Inhibiting ER Stress and UPR Activation During Adipogenic Differentiation in 3T3-L1 Cells To confirm the basic mechanism of an effect of NTP on cells, the effect of the NTP on ER stress and UPR activation during adipogenic differentiation was examined. ER stress is known to be a prerequisite for the differentiation of 3T3-L1 pre-adipocytes into adipocytes. As a result of the experiment, it was confirmed that BiP, CHOP, p-PERK, and p-eIF2 were dramatically inhibited in 3T3-L1 cells treated with the NTP on day 4, as compared to control cells not treated with the NTP. The expression levels of UPR and ER stress markers including Bip, p-IRE1, p-PERK, p-eIF2, and CHOP are increased in adipocytes at the onset of differentiation. It has recently been reported that CHOP is induced through the phosphorylation of eIF2a. Another UPR molecule, i.e., p-IRE1, was not inhibited. The results thereof are shown in FIG. 14.

In addition, the nuclear translocation of CHOP was confirmed by immunofluorescence staining. It was confirmed that the NTP treatment effectively inhibited the nuclear translocation of CHOP. These results suggest that the NTP may significantly inhibit the differentiation of pre-adipocytes into adipocytes by inhibiting ER stress and UPR activation.

Example 2. Comparison Between Obesity Treatment Effects of NTP and Direct Plasma The effects of the NTP of the present invention and direct plasma on cells were compared with each other. Direct plasma treatment was performed using the same plasma device as that used in production of the NTP, wherein plasma was generated under the same conditions, and a culture dish where cells were cultured was directly exposed to plasma.

Cells directly treated with the NTP or plasma were observed using a microscope and confirmed by Oil Red O staining. As a result of the experiment, cell proliferation was significantly inhibited both in a growth medium (GM) and a differentiation medium (DM) in the NTP-treated 3T3-L1 cells, as compared to the cells directly treated with plasma. In particular, it was confirmed that, in the case of DM, the cells directly treated with plasma were stained with Oil Red 0, which indicates intracellular lipid deposition, whereas intracellular lipid deposition was inhibited in the NTP-treated cells. These results mean that, as compared to the case of direct plasma treatment, the NTP treatment is more effective in inhibiting adipogenic differentiation and lipogenesis.

From the results of Examples 1 and 2, it was confirmed that treatment of pre-adipocytes with the NTP was significantly effective in inhibiting adipogenic differentiation and intracellular lipogenesis, and the NTP treatment exhibited a significant effect as compared to the case in which cells were directly treated with plasma.

INDUSTRIAL APPLICABILITY

The present invention relates to a composition for treating obesity, which includes liquid type plasma, and the liquid type plasma of the present invention has a significant effect of inhibiting adipogenic differentiation and reducing intracellular lipogenesis and has an effect superior to that of a case in which a subject is directly treated with plasma, and thus it is anticipated that the composition of the present invention will be greatly utilized in preventing and treating obesity.

The invention claimed is:

1. A method of producing liquid type plasma for inhibiting adipogenic differentiation, the method comprising:
 (a) filling a plasma generator with a carrier gas;
 (b) supplying a voltage of 1 kV to 20 kV and a frequency of 10 kHz to 30 kHz to the plasma generator to generate plasma; and
 (c) treating a liquid material with the generated plasma.

2. The method of claim 1, wherein, in process (a), the carrier gas comprises any one or more selected from the group consisting of nitrogen, helium, argon, and oxygen.

3. The method of claim 2, wherein the carrier gas is a mixture of helium and oxygen in a volume (vol %) ratio of 20:80.

4. The method of claim 1, wherein the treating of process (c) is performed at a distance of 0.1 cm to 15 cm from a surface of the liquid material for 1 minute per 1 ml.

5. The method of claim 1, wherein the liquid material of process (c) is water, saline, a buffer, or a medium.

6. A composition for inhibiting adipogenic differentiation, the composition comprising liquid type plasma produced using the method of claim 1.

7. A pharmaceutical composition for preventing or treating obesity, the pharmaceutical composition comprising the composition of claim 6 as an active ingredient.

8. The pharmaceutical composition of claim 7, wherein the pharmaceutical composition is in the form of an oral preparation, a parenteral preparation, or a local preparation.

9. The pharmaceutical composition of claim 7, wherein the pharmaceutical composition is used alone or in combination with surgery, radiotherapy, hormone treatment, chemotherapy, and methods using a biological response modifier.

10. A method of preventing or treating obesity, the method comprising administering the pharmaceutical composition of claim 7 to an individual.

* * * * *